United States Patent
Lei et al.

(10) Patent No.: US 11,828,706 B2
(45) Date of Patent: Nov. 28, 2023

(54) TEST SYSTEM AND METHOD FOR THE MUTUAL SOLUBILITY OF BIOMASS-BASED BLENDED FUEL

(71) Applicant: HENAN ACADEMY OF SCIENCES INSTITUTE OF ENERGY CO., LTD., Zhengzhou (CN)

(72) Inventors: Tingzhou Lei, Zhengzhou (CN); Miao Yang, Zhengzhou (CN); Zhiwei Wang, Zhengzhou (CN); Xiaofei Xin, Zhengzhou (CN); Haiyan Xu, Zhengzhou (CN); Gaofeng Chen, Zhengzhou (CN); Qian Guan, Zhengzhou (CN); Xueqin Li, Zhengzhou (CN); Yantao Yang, Zhengzhou (CN); Deyi Liang, Zhengzhou (CN); Yunhao Jia, Zhengzhou (CN); Yang Jin, Zhengzhou (CN)

(73) Assignee: HENAN ACADEMY OF SCIENCES INSTITUTE OF ENERGY CO., LTD., Zhengzhou (CN)

( * ) Notice: Subject to any disclaimer, the term of this patent is extended or adjusted under 35 U.S.C. 154(b) by 791 days.

(21) Appl. No.: 16/971,510

(22) PCT Filed: Jul. 10, 2018

(86) PCT No.: PCT/CN2018/095087
§ 371 (c)(1),
(2) Date: Aug. 20, 2020

(87) PCT Pub. No.: WO2019/144576
PCT Pub. Date: Aug. 1, 2019

(65) Prior Publication Data
US 2021/0325300 A1    Oct. 21, 2021

(30) Foreign Application Priority Data

Jan. 29, 2018    (CN) .......................... 201810081717.1

(51) Int. Cl.
*G01N 21/41*    (2006.01)
*G01N 1/20*    (2006.01)
(Continued)

(52) U.S. Cl.
CPC ....... *G01N 21/4133* (2013.01); *G01N 1/2035* (2013.01); *G01N 1/38* (2013.01);
(Continued)

(58) Field of Classification Search
CPC .... G01N 21/4133; G01N 1/2035; G01N 1/38; G01N 33/28; G01N 2001/205;
(Continued)

(56) References Cited

U.S. PATENT DOCUMENTS 7,408,632 B2    8/2008   Moore

FOREIGN PATENT DOCUMENTS

CN        201152850 Y   *  11/2008
CN        201152850 Y      11/2008
(Continued)

OTHER PUBLICATIONS

International Search Report PCT/CN2018/095087 [ISA/CN] dated Sep. 7, 2018.

*Primary Examiner* — Michael A Lyons
*Assistant Examiner* — Omar H Nixon
(74) *Attorney, Agent, or Firm* — Daniel J. Chalker; Edwin S. Flores; Chalker Flores, LLP

(57) ABSTRACT

The present invention relates to a test system and method for a biomass-based blended fuel. The system comprises a feeding device, a mixing tank, a light-sensing device, and a control device; the feeding device comprises at least two
(Continued)

fuel bottles; the fuel bottle is connected to the mixing tank by means of an oil pipe; the correspondingly connected oil pipe of each fuel bottle is provided with a flow valve; the light-sensing device comprises a laser disposed above the mixing tank, a light-reflecting mechanism disposed at the bottom in the mixing tank, and a light-sensing mechanism disposed at one side of the light reflecting mechanism; the output end of the light-sensing mechanism is signaled with the input end of the control device; the input end of the laser and the input end of the flow valve is separately signaled with the output end of the control device.

9 Claims, 2 Drawing Sheets

(51) Int. Cl.
*G01N 1/38* (2006.01)
*G01N 33/28* (2006.01)

(52) U.S. Cl.
CPC ....... *G01N 33/28* (2013.01); *G01N 2001/205* (2013.01); *G01N 2001/386* (2013.01); *G01N 2201/0638* (2013.01); *G01N 2201/06113* (2013.01)

(58) Field of Classification Search
CPC ... G01N 2001/386; G01N 2201/06113; G01N 2201/0638
See application file for complete search history.

(56) References Cited

FOREIGN PATENT DOCUMENTS

| | | |
|---|---|---|
| CN | 108037098 A | 5/2018 |
| DE | 3203882 A1 | 8/1983 |

\* cited by examiner

TEST SYSTEM AND METHOD FOR THE MUTUAL SOLUBILITY OF BIOMASS-BASED BLENDED FUEL

CROSS-REFERENCE TO RELATED APPLICATIONS

This application is the National Stage of International Application No. PCT/CN2018/095087, filed on Jul. 10, 2018, which claims priority to CN 201810081717.1, filed on Jan. 29, 2018, the contents of each of which is incorporated by reference herein.

TECHNICAL FIELD OF THE INVENTION

The invention belongs to the technical field of blended fuel testing, in particular, relates to a system for testing the mutual solubility of biomass-based blended fuels and a testing method thereof.

BACKGROUND OF THE INVENTION

The development of clean alternative fuels for automobiles can alleviate environmental pollution and reduce dependence on fossil energy has been recognized by many domestic and foreign scholars. Biomass-based liquid fuels are widely used with the advantage of sources, renewable, being easy to store, and having properties similar to fossil energy sources. In biodiesel, bioethanol, biobutnol, methyl levulinate, ethyl levulinate, propyl levulinate, and gamma valerolactone of biomass-based fuels, for examples, in the process of researching the replacement of fossil fuels, first of all, we have to carry out the mutual solubility test with fossil fuels. The mutual solubility of biomass-based blending fuels is the prerequisite for the application of biomass-based liquid fuels to internal combustion engines for vehicles. Due to diverse types of biomass-based fuels, and the complex composition, rapid and precise means of testing the range of mutual solubility between biomass-based fuels and fossil energy is of great significance for accelerating the research process of biomass-based alternative fuels. The traditional mutual solubility test method has the disadvantages of time-consuming and laborious. The development of a mutual solubility test device is a feasible method to realize the rapid test of the mutual solubility of the blended fuel.

SUMMARY OF THE INVENTION

The purpose of the present invention is to provide a system for testing the mutual solubility of biomass-based blended fuels and a testing method thereof. The system has a simple structure and is easy to operate. The principle of different refractive indexes can be used to quickly determine the mutual solubility of blended fuels.

To solve the above technical obstacles, the technical solutions adopted by the present invention are as follows:

A system for testing the mutual solubility of biomass-based blending fuels. The system includes a feeding device, a mixing tank, a light sensing device, and a control device. The feeding device includes at least two fuel bottles. The fuel bottles are connected to the mixing tank through an oil pipe. Each fuel bottle is connected with a flow valve on the corresponding oil pipe, the light-sensing device includes a laser arranged above the mixing tank, a light-reflecting mechanism arranged on the inner bottom surface of the mixing tank, and a light-sensor arranged on one side of the reflecting mechanism. The output end of the photosensitive mechanism is signally connected to the input end of the control device, and the input end of the laser and the input end of the flow valve are respectively connected to the output end of the control device.

Preferably, the reflecting mechanism is a horizontally placed reflector, the photosensitive mechanism is a plate body with a photosensitive sensor arranged on the plate surface, and the plate surface with the photosensitive sensor on the plate body is set toward the laser. The laser is at a certain angle with the vertical straight line and the laser head of the laser toward the board.

Preferably, one port of the oil pipe is connected with the corresponding fuel bottle, and the other one is connected with the end of the tee pipe, and the tee pipe is connected with the mixing tank.

Preferably, the system further includes a water bathtub, the mixing tank is located in the water bathtub, a temperature control mechanism and a first temperature detector are arranged in the water bathtub, and the output end of the first temperature detector is connected with the input end of the control device, the input end of the temperature control mechanism is connected with the output end of the control device.

Preferably, a stirrer and a second temperature detector are arranged in the mixing tank, the output end of the second temperature detector is connected to the input end of the control device, and the input end of the stirrer is connected to the output end of the control device.

Preferably, the system further includes an LED display, and the input end of the LED display is connected to the output end of the control device.

Preferably, the control device is an ECU control system.

The method of using the above-mentioned mutual solubility test system for biomass base blending fuel is as follows:

1) Under a constant temperature condition, the controlling system introduces the base fluid and additive solution into different fuel bottles, turn on the laser, the photosensitive mechanism senses the light spot reflected by the reflection mechanism through the photosensitive sensor, and use the control device to mark its position signal as the base point, then turn off the laser;

2) Quantitatively inject the base liquid into the mixing tank through the flow valve and the base liquid in the mixing tank buries the reflective mechanism. The agitator stirs the liquid in the mixing tank for a certain period of time until the liquid without bubbles. Then, turn on the laser, the photosensitive mechanism senses the light spot reflected by the reflection mechanism through the photosensitive sensor, and mark its position signal as $A_0$ through the control device, and then turn off the laser;

3) Inject the additive solution into the mixing tank by volume through the flow valve. When the liquid level in the mixing tank is calm and without bubbles, turn on the laser, the photosensitive mechanism senses the light spot reflected by the reflection mechanism through the photosensitive sensor, and controls device marks its position signal as $A_1$, and then turn off the laser;

Step 4) repeats step 3) to inject the same volume unit of additive solution into the mixing tank, and record the position signals of the corresponding light spots as $A_2$, $A_3, A_4 \ldots A_n$, the displacement relationship from $A_0$ to $A_n$ of the corresponding spot position relative to the spot position corresponding to the base point changes regularly. When the displacement relationship between the spot position corresponding to $A_{n+1}$ and the spot position corresponding to the base point changes irregularly, it represents the change in the mixing tank. Liquid stratification leads to a sudden change in the refractive index, which means that the base liquid and the additive solution are no longer mutually soluble in the current temperature state. The control device calculates the cumulative injection volume of the additive solution before stratification in the mixing tank to obtain the miscible ratio of the blended fuel.

Further, the LED displayer can display corresponding data, that is, the current temperature in the mixing tank, the addition amount of the base liquid, and the total addition amount of the additive solution to calculate the degree of mutual solubility of the base liquid and the additive solution at the current temperature.

At the same time, the test system of the present invention can also determine the relationship between the mutual solubility of the blended fuel and the ambient temperature, and the method is as follows:

1) Introduce the base liquid and additive solution into different fuel bottles respectively, turn on the laser, the photosensitive mechanism senses the light spot reflected by the reflection mechanism through the photosensitive sensor, and marks its position signal as the base point through the control device, and then turn off the laser;
2) Inject the base liquid and additive solution into the mixing tank in proportion and quantitatively through the flow valve, and make the liquid in the mixing tank bury the reflective mechanism, and turn on the laser when the liquid level in the mixing tank is calm and there are no bubbles and layers. The photosensitive mechanism senses the light spot reflected by the reflection mechanism through the photosensitive sensor, and marks its position signal as $A_0$ through the control device, and then turns off the laser;
3) Heating or cooling the mixing tank in temperature units, specifically through the temperature control mechanism of the water bathtub, when the liquid level in the mixing tank is calm and without bubbles, turn on the laser, and the photosensitive mechanism senses the reflection mechanism through the photosensitive sensor after the reflected light spot, mark its position signal as $A_1$ through the control device, and then turn off the laser;
4) repeating step 3) the operation of the same temperature gradient of the mixing tank heating or cooling units, respectively, and the temperature control signal corresponding to the recording position of the light spot $A_2$, $A_3$, $A_4$ ... $A_n$. The displacement relationship between the spot position corresponding to $A_0$ to $A_n$ and the spot position corresponding to the base point changes regularly. When the displacement relationship between the spot position corresponding to $A_{n+1}$ and the spot position corresponding to the base point changes irregularly, it represents mixed. The stratification of the liquid in the tank leads to a sudden change in refractive index, which means that the base liquid and the additive solution are no longer mutually soluble in the current temperature state. Recording the temperature information at this time can reconcile the relationship between the mutual solubility of the fuel and the temperature. The second temperature detector in the mixing tank detects the current temperature information in the mixing tank and displays the corresponding data on the LED display.

Compared with the prior art, the present invention has the following advantages: the present invention has a simple structure, uses an ECU control device to numerically control each electrical mechanism, is convenient to operate, and uses a blended fuel in a mutually soluble state and a layered state (that is, an immiscible state). The principle of different refractive index can quickly determine the mutual solubility of the blended fuel and the relationship between the mutual solubility of the blended fuel and the ambient temperature.

DETAILED DESCRIPTION OF THE INVENTION

In order to make the objectives, technical solutions and advantages of the present invention clearer, the following further describes the present invention in detail with reference to the accompanying drawings and embodiments. It should be understood that the specific embodiments described here are only used to explain the present invention, but not to limit the present invention.

Figure 1:
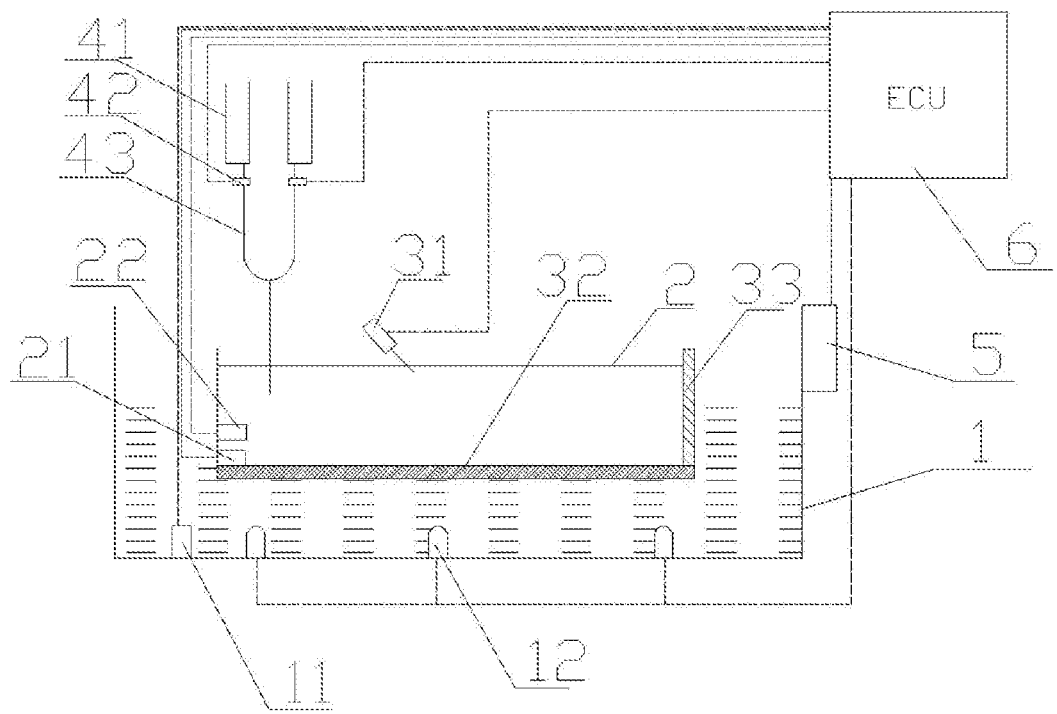
FIG. 1 is a schematic structural diagram of a system for testing the mutual solubility of biomass base blends and fuels in specific embodiments.

As shown in FIG. 1, a system for testing the mutual solubility of biomass base blend fuels, the system includes a feeding device, a mixing tank, a light sensing device, a water bathtub, an LED display 5 and a control device:

The feeding device includes two fuel bottles 41, the bottom of each fuel bottle 41 is correspondingly connected with an oil pipe, the oil pipe is connected to the mixing tank 2 through a three-way pipe 43, and each fuel bottle 41 is correspondingly connected with a volume flow valve on the oil pipe 42;

The light sensing device includes a laser 31, a light-reflecting mechanism 32, and a photosensitive mechanism 33. The laser 31 is arranged above the mixing tank 2 and arranged at a certain angle with the vertical line; the light-reflecting mechanism 32 is horizontally arranged on the mixing tank 2; the reflector on the inner bottom surface; the photosensitive mechanism 33 is a plate body with a photosensitive sensor arranged on the plate surface. The plate is arranged on the side of the reflective mechanism 32 and the plate surface with the photosensitive sensor faces the laser 31, and the laser head of the laser 31 faces the board is inclined.

The mixing tank 2 is located in the water bathtub 1, a temperature control mechanism 12 and a first temperature detector 11 are arranged in the water bathtub 1, and a stirrer 21 and a second temperature detector 22 are arranged in the mixing tank 2.

The control device is the ECU control device 6. The light sensor output end of the photosensitive mechanism 33 is signal-connected to the input end of the ECU control device 6, and the input end of the laser 31 and the input end of the volume flow valve 42 are respectively connected to the output of the ECU control device 6 of terminal signal connection. The output terminals of the first temperature detector 11 and the second temperature detector 22 are respectively connected to the input terminal of the ECU control device 6, and the input terminals of the temperature control mechanism 12 and agitator 21 are respectively connected to the output of the ECU control device 6. The input terminal of the LED display 5 is connected to the output terminal of the ECU control device 6.

Figure 2:
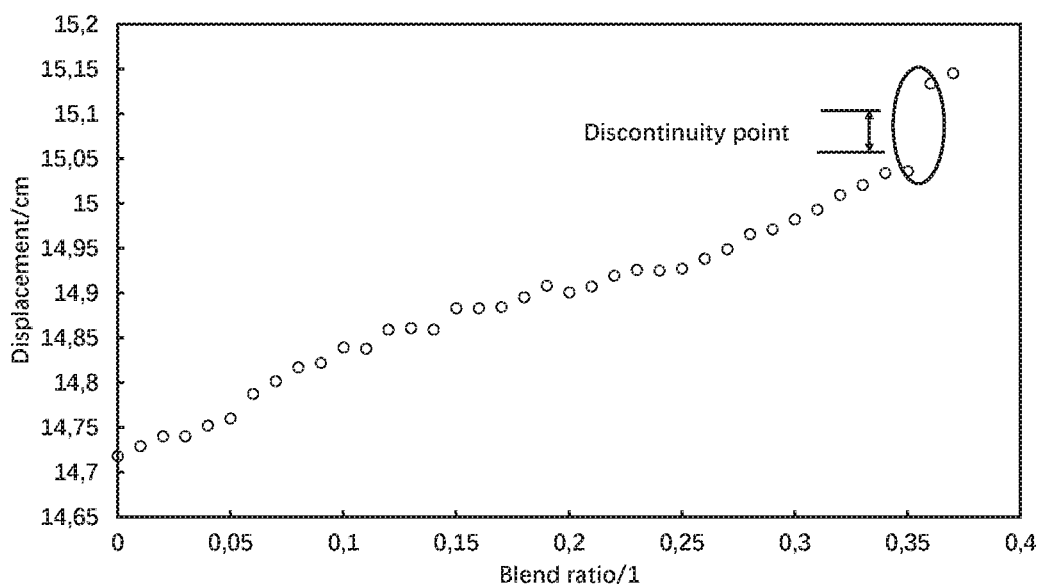
FIG. 2 is a light spot displacement diagram for measuring the miscibility ratio of gamma valerolactone and gasoline by using the mutual solubility test system of biomass-based blended fuel in a specific embodiment.

Taking γ valerolactone as an example, using the above-mentioned biomass-based blending fuel mutual solubility test system to determine the mutual solubility ratio of γ valerolactone and gasoline, the steps are as follows:

1) Introduce 200 volumes of gasoline and 200 volumes of γ valerolactone into the two fuel bottles 41 respectively. Gasoline is the base liquid, and γ valerolactone is the additive solution. Coolant is injected into the water bathtub 1, and the ECU control device 6 controls the temperature. After the mechanism 12 works and the coolant temperature reaches 20° C., the ECU control device 6 controls the laser 31 to turn on. The light beam emitted by the laser 31 is reflected by the reflective mechanism 32 to the plate of the photosensitive mechanism 33. The photosensitive sensor senses the light spot and passes the control device. Mark its position signal as the base point, and then the ECU control device controls the laser to turn off;

2) The ECU control device controls the flow valve to open and injects 100 volumes of base liquid into the mixing tank and makes the base liquid in the mixing tank bury the reflective mechanism, and wait until the second temperature detector detects that the base liquid temperature in the mixing tank reaches 20° C. and in its calm and bubble-free state, the ECU control device controls the laser to turn on. The beam emitted by the laser is refracted by the base liquid and is reflected on the plate of the photosensitive mechanism through the reflective mechanism. The photosensitive sensor senses the light spot reflected by the reflective mechanism and passes through the control device. Mark its position signal as $A_0$, and then the ECU control device controls the laser to turn off;

3) The ECU control device controls the flow valve to open and injects 1 volume of additive solution into the mixing tank. The ECU control device controls the agitator to stir the liquid in the mixing tank for a certain period of time, and the second temperature detector detects the liquid in the mixing tank. When the temperature reaches 20° C. and it is calm and bubble-free, the ECU control device controls the laser to turn on. The beam emitted by the laser is refracted by the liquid and reflected on the plate of the photosensitive mechanism through the reflective mechanism. The photosensitive sensor senses the light spot reflected by the reflective mechanism. And mark its position signal as $A_1$ through the control device, and then the ECU control device controls the laser to turn off;

4) Repeat step 3) to inject 1 volume unit of additive solution into the mixing tank, and record the position signals of the corresponding light spots as $A_2$, $A_3$, $A_4$ . . . $A_n$, $A_0$ to $A_n$ the displacement relationship between the corresponding spot position and the spot position corresponding to the base point changes regularly, and the displacement relationship between the spot position corresponding to $A_{n+1}$ and the spot position corresponding to the base point changes irregularly (as shown in FIG. 2). Time means that the liquid in the mixing tank has stratified, resulting in a sudden change in refractive index, which means that the base liquid and the additive solution are no longer mutually soluble in the current temperature state. The control device calculates the additive solution before the stratification in the mixing tank occurs. The accumulative injection volume is displayed on the LED display: ambient temperature 20° C., gasoline 100 volume units and γ valerolactone 35 volume units.

Figure 3:
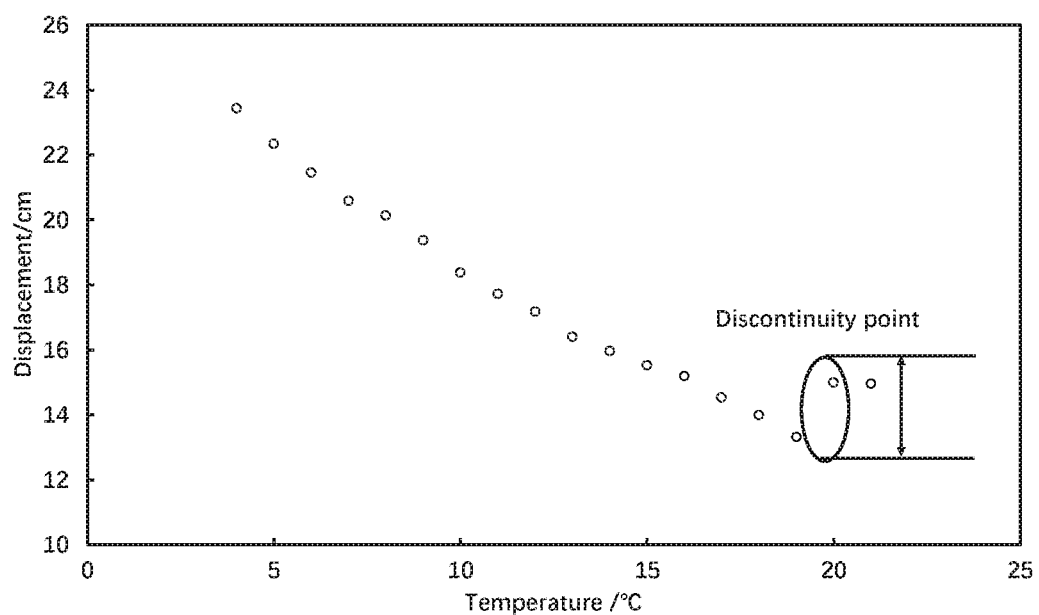
FIG. 3 is a schematic diagram of the light spot displacement measured by the mutual solubility test system of biomass-based blended fuel in a specific embodiment on the relationship between the mutual solubility of gamma valerolactone and gasoline and the environmental temperature.

The test system of the present invention can also be used to determine the relationship between the mutual solubility of the blended fuel and the ambient temperature. The method is as follows:

1) Introduce 200 volumes of gasoline and 200 volumes of γ valerolactone into the two fuel bottles respectively. The gasoline is set as the base fluid and the γ valerolactone is set as the additive solution. Coolant is injected into the water bathtub, and the ECU control device controls the temperature control mechanism. After working and making the coolant temperature reach 0° C., the ECU control device controls the laser to turn on, the beam emitted by the laser is reflected on the plate of the photosensitive mechanism through the reflective mechanism, the photosensitive sensor senses the light spot, and the control device marks its position signal as the base point. Then the ECU control device controls the laser to turn off;

2) The ECU control device controls the flow valve to open and injects the base liquid and additive solution into the mixing tank at a volume ratio of 100:35, and makes the liquid in the mixing tank bury the reflective mechanism, and wait for the second temperature detector to detect the inside of the mixing tank. When the liquid temperature reaches 0° C. and it is calm and bubble-free, the ECU control device controls the laser to turn on. The light beam emitted by the laser is refracted by the mixed liquid and reflected on the plate of the photosensitive mechanism through the reflective mechanism. The photosensitive sensor senses the reflection of the reflective mechanism. Light spot, and mark its position signal as $A_0$ by the control device, and then the ECU control device controls the laser to turn off;

3) The ECU control device controls the temperature control mechanism to work and increases the coolant temperature by 1° C. After the second temperature detector detects that the temperature of the liquid in the mixing tank reaches the corresponding temperature and is calm and without bubbles, the ECU control device controls the laser to turn on. The light beam emitted by the laser is refracted by the liquid and reflected on the plate of the photosensitive mechanism through the reflective mechanism. The photosensitive sensor senses the light spot reflected by the reflective mechanism and marks its position signal as $A_1$ through the control device, and then the ECU control device controls the laser shut down;

4) Repeat step 3) to perform a gradient heating of the mixing tank (if the base point is set at a high temperature, a gradient cooling method can also be used), and respectively record the position signals of the corresponding spots after heating as $A_2$, $A_3$, $A_4$, . . . $A_n$, $A_0$ to $A_n$ corresponding to the light spot position with respect to a $A_0$ displacement relationship of the spot positions corresponding to change regularly, to be $A_{n+1}$ corresponding to the spot position relative to $A_0$ corresponding to the spot position. When the displacement relationship changes irregularly (as shown in FIG. 3), it means that the liquid in the mixing tank has a delamination phenomenon leading to a sudden change in refractive index, which means that the base liquid and the additive solution are no longer miscible in the current temperature state, and the mixing tank. The second temperature detector inside detects the d temperature information in the mixing tank and displays the corresponding data through the LED display: temperature 20° C.

What is claimed is:

1. A system for testing the mutual solubility of biomass-based blended fuels, the system comprising:
   a feeding device;
   a mixing tank;
   a light sensing device;
   a control device;
   the feeding device includes at least two fuel bottles, and the fuel bottles pass through the tubing connected to the mixing tank, each fuel bottle is provided with a flow valve on a correspondingly connected oil pipe; and
   the light sensing device includes a laser arranged above the mixing tank, a reflecting mechanism arranged on a bottom surface of the mixing tank, and a photosensitive mechanism on one side of the reflecting mechanism, an output end of the photosensitive mechanism is signally connected to an input end of the control device, and an input end of the laser and an input end of the flow valve are respectively connected to a output end of the control device.

2. The system for testing the mutual solubility of biomass-based blended fuels according to claim 1, wherein:
   the reflecting mechanism is a horizontally placed reflector;
   the photosensitive mechanism is a plate with a photosensitive sensor on a surface of the plate an surface of the plate with the photosensitive sensor is set toward the laser; and
   the laser is set at a certain angle with a vertical line and a laser head of the laser is inclined toward the plate.

3. The system for testing the mutual solubility of biomass-based blending fuels according to claim 1, wherein one end of the oil pipe is connected to the corresponding fuel bottle, and the other end is connected to an end of a three-way pipe, and the three-way pipe is connected to the mixing tank.

4. The system for testing the mutual solubility of biomass-based blended fuels according to claim 1, further comprising:
   a water bathtub, wherein the mixing tank is located in the water bathtub;
   a temperature control mechanism and a first temperature detector are provided in the water bathtub;
   an output terminal of the first temperature detector is connected with the input end of the control device, and an input terminal of the temperature control mechanism is connected with the output end of the control device.

5. The system for testing the mutual solubility of biomass-based blended fuels according to claim 1, wherein the mixing tank is provided with a stirrer and a second temperature detector, an output end of the second temperature detector is connected to the input end of the control device, and an input end of the stirrer is connected to the output end of the control device.

6. The system for testing the mutual solubility of biomass-based blended fuels according to claim 1, further comprising an LED display, and an input end of the LED display is connected to the output end of the control device.

7. The system for testing the mutual solubility of biomass-based blended fuels according to claim 1, wherein the control device is an ECU control system.

8. A method for testing the mutual solubility of biomass-based blended fuels, the method comprising:
   1) Controlling a test system under a constant temperature condition, introducing a base liquid and an additive solution into different fuel bottles, turning on a laser, sensing a light spot reflected by a reflection mechanism through a photosensitive sensor of a photosensitive mechanism, and marking position signal as a base point through a control device, and then turning off the laser;
   2) Quantitatively injecting the base liquid into a mixing tank through a flow valve, making the base liquid in the mixing tank bury the reflective mechanism, turning on the laser when a liquid level in the mixing tank is calm and without bubbles, sensing the light spot reflected by the reflection mechanism through the photosensitive sensor of the photosensitive mechanism, marking the position signal as $A_0$ through the control device, and then turning off the laser;
   3) Injecting the additive solution into the mixing tank by volume unit through the flow valve, turning on the laser when the liquid level in the mixing tank is calm and there are no bubbles, inducing a reflection of the light spot by the reflection mechanism and sensing the reflected light spot through the photosensitive sensor of the photosensitive mechanism, marking the position signal as $A_1$ by the control device, and then turning the laser off;
   4) Repeat step 3) to inject the same volume unit of the additive solution into the mixing tank, recording the position signal of the corresponding light spot respectively of $A_2$, $A_3$, $A_4$ ... $A_n$, wherein a displacement relationship from $A_0$ to $A_n$ corresponding to the spot position changes regularly with respect to the spot position corresponding to the base point until the displacement relationship between the spot position corresponding to $A_{n+1}$ and the spot position corresponding to the base point changes irregularly, which indicates a delamination between the base liquid and the additive solution in the mixing tank leading to a sudden change in refractive index; and
   calculating a cumulative injection volume of the additive solution before the delamination in the mixing tank occurs to obtain a miscible ratio of the biomass-based blended fuel.

9. A method for testing a mutual solubility of biomass-based blended fuels, the method comprising:
   1) Introducing a base fluid and an additive solution into different fuel bottles, turning on a laser, sensing a light spot reflected by a reflection mechanism through a photosensitive sensor of a photosensitive mechanism, and marking a position signal as a base point through a control device, and then turning off the laser;
   2) Injecting the base liquid and additive solution into a mixing tank in proportion and quantitatively through a flow valve, making the base liquid in the mixing tank bury the reflective mechanism, turning on the laser when a liquid level in the mixing tank is calm and without bubbles and layering, sensing the light spot reflected by the reflection mechanism through the photosensitive sensor of the photosensitive mechanism, marking the position signal as $A_0$ through the control device, and then turning off the laser
   3) Raising or lowering a temperature of the mixing tank in units of temperature, turning on the laser when the liquid level in the mixing tank is calm and there are no bubbles, marking a position signal as $A_1$ of a light spot reflected by the photosensitive reflection mechanism by the photosensitive sensor of the photosensitive mechanism through the control device, and then turning off the laser;

4) Repeat step 3) to increase or decrease the temperature of the mixing tank with the same temperature unit gradient, and respectively record the position signal of the corresponding light spot after the temperature adjustment to $A_2, A_3, A_4 \ldots A_n$, wherein $A_0$ to $A_n$ correspond to a relative displacement of the spot position in a copolyesters $A_{n+1}$ with respect to the spot position corresponding to the base point $A_{n+1}$, and the displacement relationship of the spot position relative to the spot position corresponding to the base point changes irregularly when a stratification of the base liquid and the additive solution occurs in the mixing tank resulting in a sudden change in refractive index; and Recording a temperature information at the time of the stratification to reconcile a relationship between the mutual solubility of the biomass-based blended fuel and the temperature.

\* \* \* \* \*